United States Patent [19]

Mundt et al.

[11] Patent Number: 5,391,491

[45] Date of Patent: Feb. 21, 1995

[54] AVIAN EMBRYO CELL AGGREGATE BIOMASS FOR PRODUCING TICK-BORN ENCEPHALITIS VIRUS/VIRUS ANTIGEN

[75] Inventors: Wolfgang Mundt, Vienna; Wilfried Woehrer, Bad Voeslau; Friedrich Dorner; Johann Eibl, both of Vienna, all of Austria

[73] Assignee: Immuno Aktiengesellschaft, Vienna, Austria

[21] Appl. No.: 854,630

[22] PCT Filed: Jan. 3, 1991

[86] PCT No.: PCT/AT91/00003

§ 371 Date: Jul. 6, 1992

§ 102(e) Date: Jul. 6, 1992

[87] PCT Pub. No.: WO91/09937

PCT Pub. Date: Jul. 11, 1991

[30] Foreign Application Priority Data

Jan. 4, 1990 [AT] Austria ..................... 18/90

[51] Int. Cl.⁶ ................. C12N 5/00; C12N 5/02; C12N 7/00; A01N 1/02; C12P 21/02
[52] U.S. Cl. ................. 435/240.2; 435/240.25; 435/70.1; 435/70.3; 435/235.1; 435/1

[58] Field of Search ............. 435/1, 70.1, 70.3, 240.2, 435/240.21, 240.23, 240.25, 235.1, 948

[56] References Cited

U.S. PATENT DOCUMENTS

| 4,059,485 | 11/1977 | Tolbert et al. | 195/1.8 |
|---|---|---|---|
| 4,195,130 | 3/1980 | Hoshino et al. | 435/235 |
| 4,335,215 | 6/1982 | Tolbert et al. | 435/241 |
| 5,114,855 | 5/1992 | Hu et al. | 435/240.24 |

OTHER PUBLICATIONS

Slavik et al., "Optimized conditions of Tick-borne encephalitis virus production in vitro," *ACTA Virologica*, vol. 27, Mar. 1983.

*Primary Examiner*—Marian Knode
*Assistant Examiner*—Susan M. Dadio
*Attorney, Agent, or Firm*—Foley & Lardner

[57] ABSTRACT

The invention relates to a biomass for producing virus/virus antigen, which consists of cell aggregates having diameters of between 100 μm and 1,000 μm. The biomass according to the invention has a high metabolic activity in suspension in the culture medium and is infected with virus. It enables the large-scale production of pure virus/virus antigen and is particularly suitable for the production of TBE-virus/virus antigen.

8 Claims, No Drawings

AVIAN EMBRYO CELL AGGREGATE BIOMASS FOR PRODUCING TICK-BORN ENCEPHALITIS VIRUS/VIRUS ANTIGEN

FIELD OF THE INVENTION

The invention relates to a biomass and to a method of producing virus/virus antigen.

DESCRIPTION OF RELATED ART

Methods for producing virus/virus antigen are known. Starting materials frequently comprise so-called primary cell cultures obtained from human or animal tissues. These primary cells are infected with virus ("seed virus") and virus antigen is formed by virus propagation.

A method of propagating, for instance, tick-borne encephalitis virus (TBE-virus) is described in AT-B 358,167: chick embryo cells are suspended in cell culture medium, are infected with the virus and are used as a biomass for the production of TBE-virus antigen. To this end, the biomass is kept in suspension between one and five days under aerobic conditions at a temperature of between 25° and 38° C. Then, the cells and cell fragments are separated by centrifugation, the virus suspension obtained is inactivated by means of formalin or β-propiolacton and the virus antigen is concentrated by ultrafiltration, purified and further processed to vaccines in the usual manner.

With common preparations of primary cell cultures, it is particularly taken care that individual cells and cell aggregates as small as possible will be obtained. To reach this, the tissue must be disintegrated to the utmost extent mechanically or enzymatically. However, this treatment involves the decay of many cells. If such cell preparations are settled on the surface of suitable carrier materials, dead cells remain in the supernatant and can be removed. When using such cell preparations in suspension cultures for the production of TBE-virus antigen, there is, however, no way of separating living cells from dead or damaged cells. Consequently, the gradually occurring cell lysis results in a high degree of contamination of cell proteins in the medium, which are difficult to separate from the desired product.

Also the reproducibility of the virus/virus antigen production is low when using individual cells or small cell aggregates in suspension, because the cells may become heavily damaged, e.g., by the shearing forces created in stirring.

SUMMARY OF THE INVENTION

The invention has as its object to eliminate these disadvantages and to provide a biomass for producing virus/virus antigen, which leads to a high production output of virus/virus antigen in cultivation, is easy to handle and may be used on a commercial scale for the production of virus/virus antigen, wherein the virus/virus antigen is recoverable from the culture medium with a high purity.

The biomass according to the invention, which meets the demands pointed out above, is comprised of cell aggregates having diameters of between 100 μm and 1,000 μm, which biomass is infected with virus.

DETAILED DESCRIPTION OF THE INVENTION

The cell aggregates of the biomass according to the invention are obtained by mechanic and enzymatic treatment of human or animal tissues, wherein the tissue disintegrated in a mechanical way can be further communited to the desired size of the cell aggregates by means of a protease, such as trypsin, chymotrypsin or elastase, to further dissolve the cell aggregates.

The cell aggregates of the biomass according to the invention also may be obtained from human or animal single cells by treating the same with cell aggregating substances, such as agglutinin.

The separation of cell aggregates and single cells having diameters larger than 1,000 μm or smaller than 100 μm may be effected by screening or, preferably, by sedimentation. Compared to screening, sedimentation is simple to carry out, because sieves having pore sizes of 100 μm easily get obstructed. Moreover, no complex and expensive separators are required for sedimentation, the latter also offering advantages in terms of sterility. It has proved that the cell aggregates having diameters of between 100 μm and 1,000 μm deposit at a velocity faster than 1 cm/min, while the smaller cell aggregates deposit at a velocity of less than 1 cm/min. The separation of particles being smaller than 1,000 μm simply may be effected by screening, since there the danger of obstruction is very low.

A preferred embodiment of the biomass according to the invention is characterized in that it exhibits a high metabolic activity in suspension in the culture medium; based on the glucose consumption, this metabolic activity is 3 to 5 mg glucose per gram of biomass per hour.

The cell aggregates used to prepare the biomass according to the invention, furthermore, have the advantage that they produce large amounts of virus antigen already at an infection with a relatively small amount of seed virus. Substantially more seed virus has proved to be necessary for infecting cell aggregates smaller than 100 μm or larger than 1,000 μm in order to produce equal amounts of virus/virus antigen.

The virus/virus antigen production can be further increased by maintaining the biomass according to the invention at an oxygen concentration of at least 0.01 mmol/l preferably at at least 0.06 mmol/l, within the culture medium.

It is advantageous if the culture medium has a cell aggregate concentration of at least 10 mg cell aggregates per ml.

The biomass according to the invention is particularly suitable for the production of tick-borne encephalitis virus (TBE-virus)/virus antigen, if it consists of cell aggregates of avian embryo cells, in particular chick embryo cells, wherein the virus/virus antigen production output is further increased if an oxygen transfer rate of more than $1.60$ mmol $O_2.l^{-1}.h^{-1}$, preferably of between $1.65$ and $2.40$ mmol $O_2.l^{-1}.h^{-1}$, is adjusted.

The oxygen transfer rate (OTR), expressed in mmol $O_2.l^{-1}.h^{-1}$, is known to be a measure of the introduction of oxygen into the cell culture. The oxygen uptake rate (OUR), in turn, is a measure of the metabolic activity of a cell in general and, thus, indirectly of the virus/virus antigen synthesizing capacity of a cell.

With all the methods known today for the production of TBE-virus antigen, the specific production output of virus antigen is limited, because the presence of a large amount of infected cells in the culture medium causes a drop of its pH and, thus, an undesired inactivation of the virus titer and the destruction of the virus antigen.

It was found that the pH of such an intensively aerated culture does not drop and that a constant and high production output of virus/virus antigen can be maintained if sufficient amounts of oxygen are introduced into the culture liquid, e.g., by stirring or by means of static and/or dynamic gas distributing means.

Measurements demonstrated that TBE-virus/virus antigen production will be strongly reduced on a larger scale in a culture having a cell density of $2 \times 10^7$ cells per milliliter, that communicates with the oxygen atmosphere exclusively by its surface. By contrast, if oxygen is actively introduced into the culture, the yield of antigens can be strongly increased.

A preferred embodiment of the method according to the invention consists in that an oxygen transfer rate of more than $1.65$ mmol $O_2.1^{-1}.h^{-1}$, preferably of between $1.65$ and $2.40$ mmol $O_2.1^{-1}.h^{-1}$, is adjusted, wherein the humid cell mass optimally amounts to 30 g per liter culture medium at the most.

Experiments proved that the production of TBE-virus/virus antigen is proportional to the concentration of cell aggregates used according to the invention. The method according to the invention is feasible also with a cell aggregate concentration of less than 10 mg/ml. By contrast, it was found that a minimum concentration of 10 mg/ml is absolutely required to produce virus/virus antigen if infected single cells are cultivated.

The high seed virus titers required for infection of a primary cell culture usually are obtained only by propagation of the virus in mouse brain. By the fact that cell aggregates can be infected with a substantially slighter amount of viruses according to the invention, the seed virus required for the infection of the biomass also may be obtained from cell culture supernatants. Thereby, the chance of the mousebrain protein getting contaminated is clearly reduced.

Furthermore, it has proved that the biomass according to the invention consisting of cell aggregates of arian embryo cells also is suitable for the production of influenza, vaccinia or avipox virus antigen.

The invention will be explained in more detail by way of the following exemplary embodiments.

EXAMPLE 1

Influence of the cell aggregate size on the antigen yield.

SPF (specific pathogen free) hens' eggs were incubated at 37° C. for 12 days, tested for the actual embryo growth by a smear measuring apparatus, disinfected with alcohol and opened in a sterile box. The embryos were removed, washed and coarsely disintegrated by a cutting means. Subsequently, the enzymatic digestion of the embryonic tissue was effected by the addition of proteolytic enzymes (1 mg/embryo) at 37° C. for 20 minutes. Tissue pieces larger than 1,000 μm were separated from this tissue suspension through a sieve having a mesh size corresponding to more than 1,000 μm. Further disintegration of these cell aggregates could be reached by a sedimentation process, a sedimentation rate of $\geq 1$ cm/min being chosen as the separation criterion. To this end, the cell suspension was pumped through a sedimentation vessel from bottom to top at a flow rate of 1 cm/min. Single cells or smaller cell aggregates remained in suspension, while larger cell aggregates deposited on the bottom of the vessel. Investigations by means of sieves having different pore sizes demonstrated that the cell aggregates depositing under such conditions had a size distribution of <1,000 μm, >100 μm. Accordingly, the size of the cell aggregates remaining in suspension was <100 μm.

In this manner, three fractions of cell aggregates were obtained,
1. <100 μm
2. >1000 μm
3. <1000 μm >100 μm.

Equal biomass concentrations (30 g per liter) of these fractions were each suspended in a culture medium (Med 199) and infected with TBE-virus ($1 \times 10^5$ pfu per mg biomass). Virus propagation occurred at 37° C., the cells being kept in suspension under uniform agitation. After four days the amount of virus antigen formed was determined by means of ELISA.

In the case of fraction 1 (cell aggregates smaller than 100 μm), the virus/virus antigen production was 4.9 μg/ml; in the case of fraction 2 (cell aggregates larger than 1,000 μm) the virus/virus antigen production was 4.7 μg/ml; in the case of the fraction used according to the invention, the virus/virus antigen production was 9.3 μg/ml.

EXAMPLE 2

Influence of the cell aggregate size on the contamination with CEC (chick embryo cell) protein.

The culture media of fractions 1 and 3 obtained in Example 1 were examined for their content of CEC protein two days after the start of cultivation. The culture medium of fraction 1 contained 1.80 mg CEC protein/ml, while no more than 0.84 mg CEC protein/ml could be detected in the culture medium of fraction 3.

EXAMPLE 3

Influence of the amount of seed virus on the virus/virus antigen production.

Biomasses having cell aggregate sizes of fractions 1 and 3 were cultivated as described in Example 1 and the virus/virus antigen production was determined, four differently high amounts of seed virus ($3.2 \times 10^3$ pfu, $1 \times 10^4$ pfu, $3.2 \times 10^4$ pfu and $1 \times 10^5$ pfu, each per mg of biomass) being used for infection. The results are summarized in the following Table 1, from which it is apparent that the fraction 3 used according to the invention yields an essentially larger production of virus/virus antigen at equal amounts of seed virus.

TABLE 1

| Amount of Seed Virus for Infection | Virus/Virus Antigen Yield (μg/ml) | |
|---|---|---|
| (pfu per mg biomass) | Fraction 1 | Fraction 3 |
| $3.2 \cdot 10^3$ pfu | 2.0 μg/ml | 8.8 μg/ml |
| $1 \cdot 10^4$ pfu | 3.2 μg/ml | 10.3 μg/ml |
| $3.2 \cdot 10^4$ pfu | 5.0 μg/ml | 11.0 μg/ml |
| $1 \cdot 10^5$ pfu | 5.0 μg/ml | 11.0 μg/ml |

EXAMPLE 4

Influence of oxygen concentration on antigen production

Under the conditions indicated in Example 1, the biomass according to the invention was cultivated in the culture medium at different oxygen concentrations and the amount of virus/virus antigen was determined. The results are represented in the following Table 2, the yield of virus/virus antigen having been calculated to be 100% at an oxygen concentration of 0.06 mmol/l.

TABLE 2

| Oxygen Concentration | Yield of Virus/Virus Antigen |
|---|---|
| 0.06 mmol/l | 100% |

TABLE 2-continued

| Oxygen Concentration | Yield of Virus/Virus Antigen |
| --- | --- |
| 0.02 mmol/l | 90% |
| 0.004 mmol/l | 35% |
| 0 | 10% |

EXAMPLE 5

Influence of oxygen transfer on virus/antigen yield

Biomass having cell aggregates of fraction 3 were infected with virus as described in Example 1, were cultivated in culture vessels of different dimensions and were aearated in order to obtain different OTR-values. The suspension was maintained at a temperature of from 33° C. to 37° C. for 4 days and the yield of virus/virus antigen was determined. (Cf. Table 3).

TABLE 3

| Culture vessel | Working Volume | OTR | Virus/virus antigen yield |
| --- | --- | --- | --- |
| 0.5 l spinner (Technespinner) | 0.1 | 2.38 | 5.9 |
| | 0.3 | 0.795 | 0.97 |
| 2 l spinner (Technespinner) | 0.3 | 1.65 | 2.0 |
| | 1.0 | 0.49 | 0.32 |
| 10 l stirred flask (stirrer length 5.5 cm, 150-160 rpm) | 3.0 | 0.41 | 0.38 |
| 50 l stirred flask (stirrer length 15 cm, 80-90 rpm) | 18 | 1.10 | 0.97 |
| | 30 | 0.87 | 0.22 |
| Working volume: | liter, OTR: mmol $O_2 \cdot l^{-1} \cdot h^{-1}$, virus/virus antigen yield: µg/ml (determined by means of ELISA). | | |

From the results indicated in Table 3, it may be deduced that virus/virus antigen yields of about 5 µg/ml are attainable at an OTR of more than 2.

We claim:

1. A biomass for producing tick-borne encephalitis virus/virus antigen comprising cell aggregates of avian embryo cells, wherein said cell aggregates have diameters of between 100 µm and 1,000 µm and have been infected with tick-borne encephalitis virus.

2. The biomass of claim 1, wherein the cell aggregates are obtained by mechanical and enzymatic treatment of avian embryo tissue.

3. The biomass of claim 1, wherein the cell aggregates are obtained by treating single cells of avian embryos with cell aggregating substances.

4. The biomass of claim 1, wherein the biomass has a metabolic activity based on glucose consumption of between 3 and 5 mg of glucose consumption per gram of biomass per hour when said biomass is suspended in culture medium.

5. A method of producing tick-borne encephalitis virus/virus antigen comprising the steps of:
 (a) infecting a biomass comprised of cell aggregates of avian embryo, cells, wherein said cell aggregates have diameters of between 100 µm and 1,000 µm, with tick-borne encephalitis virus in a culture medium having an oxygen concentration of at least 0.01 mmol/l and wherein said culture medium contains at least 10 mg of cell aggregates per ml;
 (b) producing a cell aggregate mixture containing tick-borne encephalitis virus/virus antigen; and
 (c) recovering said tick-borne encephalitis virus/virus antigen from the cell aggregate mixture.

6. The method of claim 5, wherein said arian embryo cells are chick embryo cells.

7. The method of claim 5, wherein an oxygen transfer rate of more than 1.60 mmol $O_2 \cdot l^{-1} \cdot h^{-1}$ is maintained in said culture medium.

8. The method of claim 7, wherein said oxygen transfer rate is between 1.65 and 2.40 mmol $O_2 \cdot l^{-1} \cdot h^{-1}$.

* * * * *